United States Patent [19]

Korshak et al.

[11] 4,140,652

[45] Feb. 20, 1979

[54] METHOD OF PREPARING BLOOD-COMPATIBLE SORBENTS FOR RECOVERING EXO- AND ENDOGENIC POISONS

[76] Inventors: Vasily V. Korshak, ulitsa Gubkina, 4, kv. 81; Jury A. Leikin, ulitsa 8, kv. 103, both of Moscow, U.S.S.R.; Anatoly J. Neronov, bulvar Pencho Slaveikov, 13A, Sofia, Bulgaria; Ljudmila A. Tikhonova, Domodedovskaya ulitsa, 11, korpus 1, kv. 191, Moscow, U.S.S.R.; Anatoly V. Ryabov, Onezhskaya ulitsa, 45/19, kv. 33, Moscow, U.S.S.R.; Oleg V. Kabanov, ulitsa Dybenko, 38, kv. 12, Moscow, U.S.S.R.; Vitaly D. Gorchakov, Baikalskaya ulitsa, Moscow, U.S.S.R.; Nikita G. Evseev, ulitsa Muranovskaya, 10, kv. 187, Moscow, all of U.S.S.R.

[21] Appl. No.: 758,784

[22] Filed: Jan. 12, 1977

[51] Int. Cl.$^2$ ............................................. B01D 13/00
[52] U.S. Cl. .................................... 252/426; 252/428; 252/430; 252/444; 424/79; 424/83; 424/95; 424/101; 424/125
[58] Field of Search ................. 252/426, 428, 444, 430

[56] References Cited

U.S. PATENT DOCUMENTS

| | | | |
|---|---|---|---|
| 3,442,819 | 5/1969 | Herbert | 252/444 X |
| 3,983,053 | 9/1976 | Courtney et al. | 252/426 X |
| 3,996,162 | 12/1976 | McCall | 252/428 X |

*Primary Examiner*—Patrick Garvin
*Attorney, Agent, or Firm*—Steinberg & Blake

[57] ABSTRACT

A method of preparing blood-compatible sorbents for recovering exo- and endogenic poisons which comprises sorption of the blood-serum albumin on an anion exchange resin, cation exchange resin, activated carbon or a styrene and divinylbenzene copolymer with a specific surface area of at least 20 $m^2/g$. Thereafter, the sorbed albumin is subjected to polycondensation at a temperature ranging from 10° to 90° C. The method according to the present invention practically does not change the initial porous structure of the sorbents, thus ensuring sorption of such compounds as bilirubin, uric acid, creatinine, barbituric acid derivatives, potassium and ammonium ions, phenols, indoles, skatoles.

5 Claims, No Drawings

METHOD OF PREPARING BLOOD-COMPATIBLE SORBENTS FOR RECOVERING EXO- AND ENDOGENIC POISONS

The present invention relates to the synthesis of sorbents and, more specifically, to a method of preparing blood-compatible sorbents for recovering exo- and endogenic poisons.

Such sorbents are useful in clinical practice, for example, for recovering exo- and endogenic poisons from the organism by the method of hemoperfusion or sorption from various biological media and liquids as well as in combination with such apparatus as "artificially kidney" or a plasma separator.

Another field of application of such sorbents is medical industry, for example, blood conservation.

Known in the art is a method of preparing blood-compatible sorbents for recovering exo- and endogenic poisons which comprises encapsulating granules of activated carbon into semi-permeable synthetic envelopes made of nylon or polyhydroxymethylmethacrylate.

While ensuring rather high blood-compatibility of the resulting sorbents, such continous semi-permeable synthetic envelopes, including those containing thromboresistant additives, however, substantially reduce the sorption efficiency due to a limiting stage of diffusion through the membrane. Furthermore, such semipermeable membrane practically rules out the possibility of recovering metabolites of a mean molecular weight (such as bilirubin) from blood and biological media.

Such microencapsulating results in a substantial increase of the sorbent weight (up to 30%) and, consequently, reduces the sorbent capacity relative to the desired components.

It is an object of the present invention to provide a method of preparing blood-compatible sorbents ensuring efficient recovery of substances of exo- or endogenic origin from biological media and liquids.

It is another object of the present invention to provide sorbents recovering metabolites of a mean molecular weight from blood and biological media.

These and other objects of the present invention are accomplished by the provision of a method of preparing bloodcompatible sorbents for recovering exo- and endogenic poisons, which comprises adsorption of bloodserum albumin on a starting sorbent having a specific surface area of at least 20 $m^2/g$, this sorbent being an ion exchange resin, activated carbon, or a copolymer of styrene and divinylbenzene, followed by polycondensation thereof at a temperature ranging from 10° to 90° C.

It is advisable to use, as the starting sorbent, copolymers of styrene and divinylbenzene with a specific surface area over 50 $m^2/g$.

It is advisable to carry out polycondensation in the presence of a cross-linking agent, such as an aldehyde or nitrous acid, at a temperature within the range of from 10° to 40° C.

Polycondensation with aldehydes should be preferably carried out in the presence of activating agents such as aminoethanol or aminoacids taken in an amount ranging from 1 to 5 g per g of albumin.

Surface-modification of the starting sorbents by means of a high-molecular biopolymer (i.e. blood-serum albumin) by way of chemical cross-linking thereof at the sorbent surface makes it possible to ensure high compatibility of the resulting sorbents with blood, as well as to substantially reduce or completely eliminate deterioration of cellular elements of biological media and liquids upon their contact with the sorbents. The sorbents prepared by the method according to the present invention retain practically unchanged starting sorbtion characteristics in respect of such compounds as bilirubin, uric acid, creatinine, barbituric derivatives, phenols, indoles and skatoles as well as potassium, ammonium and calcium ions upon sorption from various biological liquids (blood, lymph, plasma).

The method of preparing blood-compatible sorbents for recovering exo- and endogenic poisons is preferably performed in the following manner.

Alcohol-extracted macroporous starting sorbents having a specific surface area of more than 20 $m^2/g$, such as ion exchange resin, activated carbon, copolymers of styrene and divinylbenzene containing no ionogenic groups, are standardized in solutions of inorganic acids and alkalis. Best results can be obtained with the use of macroporous ion exchange resins, such as cation exchange resins, anion exchange resins, polyampholites with a specific surface area of 30 to 50 $m^2/g$.

As copolymers it is preferred to use copolymers of styrene and divinylbenzene with a specific surface area of 50 to 100 $m^2.g$; as activated carbons it is preferred to employ those having a specific surface area of 200 to 800 $m^2/g$. Thereafter the sorbent is saturated with bloodserum albumin, preferably within 10 to 50 mg/g of the sorbent from an aqueous solution having a concentration of preferably 1-1.4% by weight at pH = 8.5-11.

The sorbed albumin is fixed at the active surface of the sorbent by way of polycondensation thereof at a temperature of 10 to 90° C. Polycondensation can be carried out in the presence of a cross-linking agent, e.g. aldehydes, nitrous acid, at a temperature of, preferably, 10° to 40° C., or without such agent at a higher temperature of 40° to 90° C. As aldehydes use is made of acetaldehyde, glutaric aldehyde, paraform, formaldehyde, the use of formaldehyde being preferred. If use is made of nitrous acid, it is possible to employ either this acid as such, or its salts of alkali metals in an acidic medium, e.g. the use of sodium nitrite in an HCl medium. Polycondensation of albumin with aldehydes is also carried out in the presence of activating agents such as aminoethanol or amino acids (preferably glycine) taken in an amount of 1 to 5 g per g of albumin.

The reaction of polycondensation using aldehydes is conducted either within the pH range of from 3 to 4 (for cation exchange resins) or within the range of from 8.5 to 11 (for anion exchange resins, activated carbons, copolymers containing no ionogenic groups).

Fixation of albumin is also effected in the presence of nitrous acid by the reaction of diazo coupling with sodium nitrite in an acidic medium (pH = 3-4), using sodium nitrite in the amount of 2 g per g of albumin.

The reaction of albumin polycondensation at the sorbent active surface is conducted at a temperature within the range of from 20° to 40° C., whereby the native structure of the protein component remains unchanged.

Higher temperatures of 40° to 90° C. can be used when treating albumin sorbed on strongly acidic and strongly basic ion exchange resins, preferably on strongly acidic cation exchange resins.

The blood-compatible sorbents prepared by the method according to the present invention have been tested in clinical conditions for treating mechanical jaundice and hepatic insufficiency; for correction of hyperkaliemia with patients suffering from chronic renal insufficiency, as well as for treating poisonings with barbituric aid derivatives.

The blood-compatible anion exchange resin has been clinically tested for treatment of patients suffering from mechanical jaundice and hepatic insufficiency. The results obtained show that hemosorption with the blood-compatible anion exchange resin reveals a clearly pronounced clinical effect, i.e. the patients feel better, dermal itching disappears; in some cases the hypertrophic liver dimensions are decreased; appetite is also better; bilirubin level is reduced by 1.5-2 mg%, on the average, per seance of hemosorption.

Morphologic investigations revealed no change in the level of thrombocytes, leukocytes, erythrocytes and lymphocytes upon the contact of the diseased blood with the sorbent. Hemodynamic characteristics and physiological parameters remained stable during the hemosorption. Improvement of the health condition of the patients after the hemosorption made it possible to perform surgical intervention under favourable conditions.

The blood-compatible cation exchange resin has been clinically tested for correction of hyperkaliemia with patients suffering from chronic renal insufficiency and assigned to regular hemodialysis. Tests have shown that a 2-hours' seance of hemosorption makes it possible to efficiently cut short hyperkaliemia, thus providing an opportunity to avoid extraordinary seances of hemodialysis with this category of patients. No negative side effects have been revealed in the course of hemosorption; neither has deterioration of thrombocytes, erythrocytes and leukocytes upon the blood contact with the sorbent been observed.

The blood-compatible activated carbon has been employed for treating acute poisonings with barbituric acid compounds. Clinical tests of the sorbent have shown its effectiveness for curing acute intoxications. Two-three 1-hour seances of hemosorption performed in succession one after another made it possible to take a patient out of a heavy barbituric coma of III-IV stages or to convert it to a lesser-stage coma.

Level of barbiturates in the total blood flow during the one-hour hemoperfusion on activated coal modified according to the present invention has been reduced by 20 to 40%.

The results of clinical tests performed with an activated blood-compatible carbon for treating acute poisonings makes it possible to state that hemosorption using this particular sorbent is, at the time being, the most suitable method enabling, unlike other treating methods, a lowered mortality rate of patients being in a heavy III-IV stage barbituric coma.

The blood-compatible activated carbon has been also used for the removal, from the blood of patients suffering from chronic renal insufficiency, of creatinine and uric acid. The clinical tests have shown that the 2-hours' hemosorption is equivalent, in respect of the amount of the substances being removed (creatinine and uric acid) as well as its clinical effect, to a 6-8 hours' seance of hemodialysis which enables the use of hemosorption on a blood-compatible activated carbon as a supplementary, to hemodialysis, procedure for patients suffering from chronic renal insufficiency and assigned to regular hemodialysis.

In the course of hemosorption performed using a blood-compatible carbon according to the present invention no substantial change in the level of thrombocytes, leukocytes and erythrocytes in the total blood flow has been observed and the level of free hemoglobin also remained unchanged; no negative side effects have been observed.

The sorbents prepared by the method according to the present invention do not break blood form elements and cause no negative side phenomena in the course of hemosorption (arterial pressure drop; rigor; feeling of discomfort).

Chemical binding of albumin at the active surface of the sorbents in amounts of from 40 to 60 mg per g of the sorbent ensures its durable fixation on the sorbents thus eliminating the possibility of washing-out of albumin and its entraining with blood as well as avoiding pyrogenic reactions during hemoperfusion. The use of aldehydes in a concentration of from 4 to 6% by weight provides the opportunity of preparing sorbents which are sterile right after the synthesis thereof. Additional sterilization of the blood-compatible sorbents may be effected by autoclaving (for cation exchange resins) as well as by gamma-irradiation with a dose of up 3 MRad (for cation exchange resins, anion exchange resins, polyampholites, activated carbons, cpolymers containing no ionogenic groups).

The method of producing blood-compatible sorbents according to the present invention does not change their starting porous structure and specific surface area; it does not provide for a continuous coating thus ensuring a highly-effective sorption process in respect of certain metabolites having a mean molecular weight (for example, bulirubin). Thus, a 150 ml column containing a blood-compatible anion exchange resin can recover from blood up to 70 mg of bilirubin (with the starting concentration of bilirubin in blood of about 20 mg% and hemoperfusion time of 45 min). A 200 ml column packed with a blood-compatible cation exchange resin recovers from blood up to 30 mg. equiv. of potassium ions or up to 2 mg. equiv. of ammonium ions.

A 150 ml column containing a blood-compatible activated carbon recovers from blood up to 110 mg of a mixture of barbituric acid derivatives for 40 minutes of hemosorption at the initial concentration of about 8 mg% or up to 280 mg of luminal for 40 minutes of hemosorption at the initial concentration of about 10 mg%.

A 400 ml column packed with modified activated carbon can recover from blood up to 440 g of creatinine for 40 minutes of hemosorption at the initial concentration of about 13 mg% and up to 260 mg of uric acid at the initial concentration of about 8 mg%.

For a better understanding of the present invention some specific examples illustrating the method of producing blood-compatible sorbents for recovering exo- and endogenic poisons are given hereinbelow.

EXAMPLE 1

To prepare a blood-compatible anion exchange resin, a copolymer of styrene with 20% by weight of divinylbenzene having specific surface area of 100 m$^2$/g and prepared in the presence of 80% by weight of isooctane is treated with methylchloride and aminated with trimethylamine (static exchange capacity as measured by 0.1N HCl is 4.5 mg.equiv/g.). The anion exchange resin is washed with distilled water, a 3% aqueous solution of HCl, distilled water and then extracted with ethanol (5 l per kg of the anionite), then again washed with distilled water and a 3% aqueous solution of NaOH. The anion exchange resin is added to 2 l of a 1.2% aqueous solution of albumin and stirred at room temperature and a pH value of 10-11 for a period of from 6 to 8 hours. Thereafter, the mixture is added to 0.3 l of a 37% aqueous solution of formaldehyde and stirred at room temperature at a pH value of 10-11 for 20 hours. On completion of the reaction, the sorbent is separated from the liquid phase and washed with a sterile physiological solution till no formaldehyde is detected in the washings and the eluate pH equal to 7.4.

The anion exchange resin prepared by the above-described procedure has a high compatibility with blood.

Thus, during hemosorption on dogs with simulated acute hepatic insufficiency the number of thrombocytes in the total blood flow remains practically unchanged: 40,000 in $mm^3$ prior to hemosorption and 44,000 in $mm^3$ after 45 minutes of hemoperfusion. In the case of a healthy dog the level of thrombocytes, after 60 minutes of hemoperfusion, is changed from 84,000 to 79,000 in $mm^3$.

The sorbent has been used in the treatment of patients suffering from mechanical jaundice and hepatic insufficiency.

The results of clinical tests have proven the experimental data: the level of thrombocytes in the total blood flow of the patients is equal, prior to hemosorption (in thousands) to $131 \pm 27$; after 45 minutes of hemoperfusion it is equal to $110 \pm 30$ (for 6 patients)

For 45 minutes of hemosorption a 150 ml column absorbs up to 70 mg of bilirubin from the blood. The number of erythrocytes and leukocytes in the total blood flow of the patients remains practically unchanged in the course of hemosorption.

EXAMPLE 2

To prepare a blood-compatible cation exchange resin, a copolymer of styrene and 20% by weight of divinylbenzene having a specific surface area of 100 $m^2/g$ and produced in the presence of 80% by weight of isooctane, followed by treatment with phosphoric trichloride, hydrolysis and oxidation of the reaction product with nitric acid (static exchange capacity with respect to 0.1N of NaOH is 7.6 mg.equiv./g.) is washed with distilled water, a 3% aqueous solution of NaOH and again distilled water. The cation exchange resin is extracted with ethanol (5 liters per kg of the sorbent), washed with distilled water and a 3% aqueous solution of hydrochloric acid. The cation exchange resin is added to a 1.4% aqueous solution of albumin (2 liters per kg of the sorbent) and agitated at a pH = 3-4 at room temperature for a period of from 6 to 7 hours. The reaction mixture is added to 0.36 liter of a 37% aqueous solution of formaldehyde, temperature is raised to 38° C and stirring of the reaction mass is continued for 9-10 hours at a pH value of 3-4. On completion of the reaction, the sorbent is separated from the reaction mass and washed with a sterile physiological solution exempted from ammonium ions till the eluate has a pH value of 7.4 and there is an absence of formaldehyde in the eluate.

Experiments performed on dogs with simulated hepatic insufficiency have revealed that no thrombocytes are broken in the course of hemosorption (68,000 in $mm^3$ prior to hemosorption and 64,000 in $mm^3$ after hemosorption for 60 minutes). A 200 ml column recovers for 60 minutes up to 2 mg. equiv. of ammonium ions from the blood.

EXAMPLE 3

To prepare a blood-compatible anion exchange resin, a copolymer of 4-vinylpyridine with 10% by weight of divinylbenzene, produced in the presence of 80% by weight of isooctane and having a specific surface area of 30 $m^2/g$ is reacted with methyl iodide (static exchange capacity with respect to $SO''_4$ ion, 8 mg.equiv./g.) is washed with distilled water, a 3% aqueous solution of hydrochloric acid and then again with distilled water. Then the product is extracted with ethanol (6 liters per kg of the anion exchange resin), washed with distilled water and a 2% aqueous solution of sodium bicarbonate.

The anion exchange resin is added to a 1.3% aqueous solution of albumin (at the rate of 2 liters per kg of the anion exchange resin) and agitated at a pH value of 8.5-9 for a period of from 9 to 10 hours. Thereafter, the mixture is added to 0.35 liter of a 25% aqueous solution of glutaric aldehyde and 55 g of glycine. The reaction mixture is stirred at room temperature for a period of from 8 to 9 hours maintaining a pH = 8.5 - 9. On completion of the reaction, the sorbent is separated from the reaction mass and washed with a sterile physiological solution until the eluate pH equal to 7.4.

Investigations performed on dogs with simulated acute hepatic insufficiency have shown that no breaking of thrombocytes is observed upon contacting blood with the sorbent prepared by the method according to the present invention (20,000 in $mm^3$ prior to hemoperfusion and 24,000 in $mm^3$ after 50 minutes of hemoperfusion).

EXAMPLE 4

To prepare a blood-compatible anion exchange resin, a copolymer of styrene with 20% by weight of divinylbenzene, produced in the presence of 80% by weight of isooctane and having a specific surface area of 120 $m^2/g$, treated with methylchloride and aminated with dimethylethanolamine (static exchange capacity with respect to 0.1N HCl is 3.0 mg.equiv./g), whereafter it is washed with distilled water. Then the product is extracted with ethanol (at the rate of 4 liters per kg of the anion exchange resin), again washed with distilled water and a 3% solution of NaOH. The anion exchange resin is added to a 1.2% aqueous solution of albumin (at the rate of 2 liters per kg of the sorbent), stirred for a period of 10 to 12 hours, while maintaining the pH = 9-10, and the mixture is added to 0.3 l of a 37% aqueous solution of formaldehyde. The reaction mass is stirred for a period of from 12 to 14 hours while maintaining pH = 9.3-10.5. The sorbent is then separated, washed with a sterile physiological solution until no formaldehyde is detected in the eluate and the pH of the latter is 7.4.

During hemosorption with the use of the thus-prepared anion exchange resin, in total blood flow of dogs with simulated acute hepatic insufficiency no decrease in the level of thrombocytes is observed (12,000 in $mm^3$ prior to hemoperfusion and 15,000 in $mm^3$ after 60 minutes of hemoperfusion).

EXAMPLE 5

To prepare a blood-compatible cation exchange resin, a copolymer of styrene with 20% by weight of divinylbenzene and, produced in the presence of 80% by weight of iso-octane (specific surface area 100 $m^2/g$) is sulphated with sulphuric acid (static exchange capacity for 0.1N NaOH is 4.8 mg.equiv./g), washed with distilled water, a 3% of aqueous NaOH solution and again with distilled water. Then, the product is extracted with ethanol (7 liters per kg of the cation exchange resin), washed with distilled water and a 3% aqueous solution of hydrochloric acid. The cation exchange resin is added to a 1.4% solution of albumin (2 liters per kg of the sorbent) and stirred for a period of 7 to 8 hours at a pH value of 3-4. Then, 130 g of paraform are added thereto, and the temperature is elevated to 40° C; the mixture is stirred for 10 to 12 hours while maintaining pH = 3-4. The sorbent is separated from the reaction mixture and washed with a sterile physiological solution until the pH = 7.4 and there are no formaldehyde traces in the washings.

In the experiments performed on dogs with simulated renal insufficiency and hyperkaliemia no deterioration of thrombocytes is observed during hemosorption (114,000 in mm$^3$ prior to hemoperfusion and 100,000 in mm$^3$ after 60 minutes of hemoperfusion). A 200 ml column recovers up to 30 mg.equiv. of potassium ions from the dog blood.

EXAMPLE 6

Sulphocation exchange resin in H$^+$ form is extracted and prepared as described in Example 5. The cation exchange resin is added to a 1% solution of albumin (1.5 l per kg of the sorbent) and kept at room temperature for 12 hours. The albumin solution is decanted, the cation exchange resin is washed with a 10% solution of NaCl (3 l per kg of the sorbent), then the solution is decanted and 10% solution of NaCl (2 l per kg of the sorbent) is added, heated to 90° C, the sorbent is kept in this solution for 5 hours under stirring. A 1-hour hemoperfusion on a dog with ligated urinary ducts resulted in a 20 ± 15% change in the level of thrombocytes against the background of 185,000 in mm$^3$.

EXAMPLE 7

To prepare a blood-compatible cation exchange resin, a copolymer of methacrylic acid with 10% by weight of divinylbenzene (static exchange capacity for 0.1N NaOH is 10 mg.equiv./g) is washed with distilled water, a 3% aqueous solution of NaOH, again with distilled water and then extracted with ethanol (5 liters per kg of the cation exchange resin). Then the cation exchange resin is washed with a 3% aqueous solution of HCl and added to a 1.4% aqueous solution of albumin (2 liters per kg of the cationite) and stirred for a period of from 14 to 16 hours at a pH value of 3-4 at room temperature. The reaction mass is added to 1.5 l of a 10% aqueous solution of acetaldehyde, the reaction temperature is elevated to 38° C and the mixture is stirred for 9-10 hours while maintaining pH within the range of 3 to 4. Thereafter, the resulting sorbent is separated and washed with a sterile physiological solution until the pH = 7.4 and there is absence of acetaldehyde in the washings. The cation exchange resin prepared by the method according to the present invention breaks no thrombocytes during hemoperfusion (90,000 in mm$^3$ prior to hemoperfusion and 92,000 after hemoperfusion) in the total blood flow of a healthy dog.

EXAMPLE 8

To prepare a blood-compatible sorbent, a copolymer of styrene with 20% by weight of divinylbenzene, produced in the presence of 80% by weight of isooctane and having a specific surface area of 80 m$^2$/g is extracted with ethanol (4 liters per kg of the sorbent), and washed with a 3% aqueous solution of HCl. The sorbent is added to a 1.2% aqueous solution of albumin (2 liters per kg of the sorbent) and stirred for a period of 12 to 14 hours at room temperature and a pH value of 9-10. Thereafter, the product is added to 100 g of monoethanolamine, stirred for 30 minutes, added to 0.3 liter of a 37% aqueous solution of formaldehyde and stirred at room temperature and a pH value of 9-10 for a period of from 16 to 18 hours. The resulting sorbent is separated from the reaction mixture and washed with a sterile physiological solution until the pH = 7.4 of the eluate and there is an absence of formaldehyde therein.

The sorbent prepared by the method according to the present invention results in no breaking of thrombocytes during hemosorption when contacted with blood of dogs with simulated acute hepatic insufficiency (initial number of thrombocytes is 38,000 in mm$^3$ and after 90 minutes of homoperfusion the number of thrombocytes is 40,000 in mm$^3$).

EXAMPLE 9

A copolymer of styrene with 15 wt.% of divinylbenzene, produced in the presence of 100 wt.% of isooctane and having a specific surface area of 100 m$^2$/g, is extracted with ethyl alcohol (3 l per kg of the sorbent). The copolymer is added to a 1% aqueous solution of albumin (3 l per kg of the sorbent) and stirred at room temperature for 10 hours at pH = 8-9. The 0.2 l of a 37% aqueous solution of formaldehyde and 100 g of monoethanolamine are added per kg of the copolymer and stirred at room temperature for 20 hours. The resultant sorbent is washed with distilled water until there are no traces of formaldehyde and with a sterile physiological solution until the eluate pH is 7,4 ± 0.1.

The sorbent thus prepared causes no trauma of the form elements in experiments on dogs with one hour perfusion through a column with 150 ml of the sorbent at a rate of 80 ml/min.

The initial level of thrombocytes is 82,000 in mm$^3$; after hemosorption it is 84,000 in mm$^3$. The sorbent recovers chlorinated hydrocarbons and higher alcohols from blood.

EXAMPLE 10

A copolymer of styrene with 5 wt.% of divinylbenzene, produced in the presence of 15 wt.% of isooctane and having a specific surface area of 50 m$^2$/g, is treated as described in Example 9.

Perfusion on dogs showed no trauma of thrombocytes. Change in the level of thrombocytes in the course of a one-hour perfusion was 10 ± 10% with a probability of not less than 0.95.

EXAMPLE 11

To prepare a blood-compatible sorbent, an activated carbon prepared from coco-nut shells with steam activation (total pore volume is 0.816 cm$^3$/g; micropore volume is 0.461 cm$^3$/g; transitional pore volume is 0.054 cm$^3$/g and macropore volume is 0.301 cm$^3$/g) is washed with tap water to remove dust and then washed with distilled water. Then the coal is extracted with ethanol (at the rate of 3 liters per kg of the carbon), added to a 1% aqueous solution of albumin (1 liter per kg of the carbon) and agitated for a period of 12 to 14 hours at room temperature maintaining pH = 9.5–10.5. Then the mixture is added to 0.2 liter of a 37% aqueous solution of formaldehyde and stirred for a period of from 20 to 22 hours at room temperature while maintaining pH value within the range of from 10 to 11. On completion of the reaction the sorbent is separated, washed with a sterile physiological solution until the pH = 7.4 and there is an absence of formaldehyde in the eluate.

The modified activated carbon prepared by the method according to the present invention features a high compatibility with blood. Upon hemosorption on dogs with simulated acute hepatic insufficiency the number of thrombocytes in the total blood flow is substantially constant: 180,000 in mm$^3$ prior to hemosorption and 160,000 in mm$^3$ after 45 minutes of hemoperfusion.

The sorbent has been employed for treating patients suffering from acute barbituric poisoning and chronic renal insufficiency. The level of thrombocytes in the total blood flow prior to hemosorption and after 40 minutes of hemosorption is respectively 62,000 and 60,000 in mm$^3$. A 150 ml column absorbs from the blood for 40 minutes up to 100 mg of barbiturates (mixtures of barbituric acid derivatives); a 400 ml column absorbs up to 390 mg of creatinine and up to 210 mg of uric acid. The number of erythrocytes and leukocytes in the total blood flow of the patients remains practically unchanged during the hemosorption.

EXAMPLE 12

To prepare a blood-compatible sorbent, an activated carbon produced from turf with activation by means of potassium sulphide (total pore volume is 1.11 cm$^3$/g; micropore volume is 0.60 cm$^3$/g; transitional pore volume 0.28 cm$^3$/g; macropore volume is 0.23 cm$^3$/g) is washed with tap water to remove dust and then washed with distilled water. Thereafter, the carbon is extracted with ethanol (5 liters per kg of the sorbent), added to a 1% aqueous solution of albumin (1 liter per kg of the carbon) and agitated for a period of 12 to 14 hours at room temperature and a pH value of from 9.5 to 10.5. Then the mixture is added to 0.2 l of a 25% aqueous solution of glutaric aldehyde; the reaction temperature is elevated to 38° C and the reaction is conducted under stirring for a period of from 8 to 10 hours while maintaining pH = 8.5–9.

The resulting sorbent is separated from the reaction mass and washed with a sterile physiological solution until the pH = 7.4 and there is an absence of glutaric aldehyde in the washings.

The sorbent prepared by the method according to the present invention features a high blood-compatibility. Upon hemosorption on healthy dogs the number of thrombocytes in the total blood flow remains practically unchanged: 60,000 in mm$^3$ prior to hemosorption and 65,000 in mm$^3$ - after 40 minutes of hemosorption.

The modified activated carbon has been employed for treating patients suffering from poisoning with mixtures of barbiturates, and patients with chronic renal insufficiency. Clinical tests have proven the experiment results: the level of thrombocytes hemosorption to hemosportion is 110,000 in mm$^3$; after 40 minutes of hemosorption it remains unchanged, i.e. 110,000 in mm$^3$. For 40 minutes of hemosorption a 150 ml column absorbs from the blood up to 110 mg of barbiturates (mixtures of barbituric acid derivatives); a 400 ml column absorbs up to 440 mg of creatinine and up to 260 mg of uric acid. During hemosorption the number of erythrocytes and thrombocytes in the total blood flow of the patients remains practically unchanged.

EXAMPLE 13

To prepare a blood-compatible sorbent, activated carbon produced from graphitized carbon black and activated at a temperature of 3,000° C, having a specific surface area of 20 m$^2$/g as determined by the BET (Brunauer-Emmet-Teller) method, is washed with distilled water. Then the carbon is extracted with ethyl alcohol (300 ml per 100 g of the carbon), added to a 1% aqueous solution of albumin (100 ml per 100 g of the carbon) and stirred for 10 hours at pH = 10 at room temperature. Then 0.2 l of a 37% aqueous solution of formaldehyde is added to the mixture, and stirring is conducted for 20 hours at room temperature and pH maintained at 10. On completion of the reaction the sorbent is separated and washed with a sterile physiological solution to pH = 7.4 and no traces of formaldehyde in the eluate.

The modified activated carbon prepared by the abovedescribed method features satisfactory compatibility with blood. In case of hemosorption on dogs with simulated acute hepatic insufficiency the number of thrombocytes in the total blood flow changes from 220,000 in mm$^3$ prior to hemosorption to 150,000 in mm$^3$ after 40 minutes of hemoperfusion.

EXAMPLE 14

To prepare a blood-compatible cation exchange resin, a copolymer of styrene with 20% by weight of divinylbenzene prepared in the presence of 80% by weight of isooctane is sulphurated by means of sulphuric acid (static isooctane capacity for 0.1N NaOH is 5.0 mg.equiv./g), washed with distilled water, a 3% aqueous solution of NaOH and again with distilled water. Then the product is extracted with ethanol (5 liters per kg of the cationite), washed with distilled water and a 3% aqueous solution of HCl. The cationite is then added to 1.2% aqueous solution of albumin (2 liters per kg of the cation exchange resin) and stirred for 12 to 14 hours at room temperature and a pH value of 3 to 4.40 g of sodium nitrite are dissolved in 0.5 liter of distilled water and the solution is gradually added to the reaction mixture while controlling the pH value. The reaction is conducted under stirring at a pH within the range of from 3 to 4 at room temperature for a period of from 18 to 20 hours. The resulting sorbent is separated from the reaction mixture and washed with a sterile physiological solution to the pH = 7.4 and absence of nitrite ions in the eluate.

The sorbent prepared by the method according to the present invention has been tested on dogs with simulated hyperkaliemia and renal insufficiency. A 200 ml column recovers from the blood up to 25 mequiv. of potassium with no thrombocytes broken (the initial number of thrombocytes in the total blood flow of the dog prior to hemosorption is 142,000, after 120 minutes of hemosorption the number of thrombocytes is equal to 151,000).

EXAMPLE 15

To prepare a blood-compatible cation exchange resin, a copolymer of styrene with 20% by weight of divinylbenzene, produced in the presence of 80% by weight of isooctane and having a specific surface area of 100 m$^2$/g is treated with phosphorus trichloride; the reaction product is hydrolyzed (static exchange capacity for 0.1N NaOH is 3.8 mg.equiv./g), washed with distilled water and a 3% aqueous NaOH solution, again with distilled water and extracted with ethanol (5 liters per kg of the cation exchange resin). The cation exchange resin is washed with distilled water, a 3% aqueous solution of HCl and then added to a 1.2% aqueous solution of albumin (2 liters per kg of the cation exchange resin). The mixture is stirred for a period of 6 to 8 hours at room temperature while maintaining pH equal to 3-4. Then the reaction mass is gradually added to 0.5 liter of a 8% aqueous solution of sodium nitrite and the reaction is conducted for a period of from 16 to 18 hours at the temperature of 38° C and pH = 3-4. The resulting sorbent is separated and washed with a sterile physiological solution until the pH = 7.4 and there is an absence of nitrite ions in the eluate.

The sorbent prepared by the method according to the present invention has been tested on dogs with simulated hepatic insufficiency. A 200 ml column recovers from the blood up to 3.2 mg.equiv. of ammonium ions; during a 60 minutes' hemoperfusion no breaking of thrombocytes is observed (96,000 in $mm^3$ prior to hemosorption and 92,000 in $mm^3$ after hemosorption).

EXAMPLE 16

To prepare a blood-compatible sorbent, an activated carbon based on coal dust and wood gum and activated by steam (total pore volume is 0.70 $cm^3/g$, micropore volume is 0.33 $cm^3/g$, transition pore volume is 0.07 $cm^3/g$; macropore volume is 0.30 $cm^3/g$) is washed with tap water to remove dust and then with distilled water. Afterwards, the carbon is extracted with ethanol (5 liters per kg of the coal) and added to a 1% aqueous solution of albumin (1 liter per kg of the coal) and agitated for a period of 12 to 14 hours at a pH value of 3 to 4 and room temperature. Then the mixture is gradually added to 0.4 l of a 8% aqueous solution of $NaNO_2$ and stirred at room temperature for a period of from 20 to 24 hours while maintaining pH = 3 to 4. On completion of the reaction, the sorbent is separated and washed with a sterile physiological solution until the pH = 7.4 and there is an absence of nitrite ions in the eluate.

The modified activated coal prepared by the method according to the present invention features a high compatibility with blood. In the course of hemosorption on a healthy dog the number of thrombocytes in the total blood flow remains substantially unchanged: 260,000 in $mm^3$ prior to hemosorption and 240,000 in $mm^3$ after 40 minutes of hemoperfusion.

The modified activated carbon has been employed for treatment of patients suffering from acute barbituric poisoning and chronic renal insufficiency. The level of thrombocytes in the total blood flow of the patient prior to hemosorption is 200,000 in $mm^3$, after 40 minutes of hemosorption it is 180,000 in $mm^3$. For 40 minutes a 150 ml column absorbs from the blood up to 80 mg of barbiturates (mixtures of barbituric acid derivatives).

A 400 ml column absorbs up to 350 mg of creatinine and up to 160 mg of uric acid. The number of erythrocytes and leukocytes in the total blood flow of the patients during hemosorption remains substantially unchanged.

EXAMPLE 17

To prepare a blood-compatible polyampholite, a copolymer of styrene and 2.5 - methylvinylpyridine in a molar ratio of 60; 40 with 20 parts by volume of divinylbenzene and 80 parts by volume of isooctane having a specific surface area of 30 $m^2/g$ is phosphorylated and washed by following the procedure described in Example 2 (static exchange capacity with respect to 0.1N NaOH is 3 mg.equiv/g, static exchange capacity with respect to 0.1N HCl is 1.3 mg.equiv./g). The polyampholite is added to 2 liters of a 1.3% solution of albumine (per kg of the polyampholite), 0.55 l of a 25% solution of glutaric aldehyde and 50 g of glycine. The reaction mixture is stirred at a temperature of 30° C for 8 to 9 hours, and then washed with a sterile physiological solution until the pH at the column outlet is equal to 7.4.

In case of a one-hour perfusion on dogs with simulated acute hepatic insufficiency the number of thrombocytes in arterial blood is before perfusion, 102,000 in $mm^3$ and after perfusion, 95,000 in $mm^3$.

What is claimed is:

1. A method of preparing blood-compatible sorbents for recovering exo- and endogenic poisons comprising sorption, on a starting sorbent with a specific surface area of at least 20 $m^2/g$, selected from the group consisting of ion exchange resins, activated carbon and a copolymer of styrene and divinylbenzene, of blood-serum albumin and subsequent polycondensation thereof on said sorbent at a temperature ranging from 10° to 90° C.

2. A method as claimed in claim 1, wherein as the starting sorbent use is made of copolymers of styrene and divinylbenzene, with a specific surface area of more than 50 $m^2/g$.

3. A method as claimed in claim 1, wherein polycondensation is carried out in the presence of a cross-linking agent selected from the group consisting of an aldehyde and nitrous acid at a temperature of 10° to 40° C.

4. A method as claimed in claim 1, wherein the polycondensation with aldehydes is conducted in the presence of activating agents selected from the group consisting of aminoethanol and aminoacids taken in an amount ranging from 1 to 5 g per g of albumin.

5. Blood-compatible sorbent produced according to the method of claim 1.

* * * * *